United States Patent [19]
Dreyer et al.

[11] Patent Number: 6,020,995
[45] Date of Patent: Feb. 1, 2000

[54] FOLDING RACK FOR MICROSCOPE SLIDES

[75] Inventors: Dale A. Dreyer, Vadnais Heights; Benjamin L. Behler, Maplewood, both of Minn.

[73] Assignee: Systec Inc., New Brighton, Minn.

[21] Appl. No.: 09/079,794

[22] Filed: May 15, 1998

[51] Int. Cl.[7] .......................... G02B 21/34; B65D 85/48
[52] U.S. Cl. ...................... 359/396; 359/398; 206/454; 436/46
[58] Field of Search ..................... 359/391–398; 206/308.1, 308.3, 454–456; 436/46, 48; 422/58, 68.1, 99, 102–104; 211/40, 41.12, 41.4, 149

[56] References Cited

U.S. PATENT DOCUMENTS

| | | | |
|---|---|---|---|
| 595,516 | 12/1897 | Baird | 211/132.4 |
| 902,153 | 10/1908 | Logan | 206/456 |
| 1,035,552 | 8/1912 | Doering, Jr. | 211/55 |
| 1,274,306 | 7/1918 | Moisson | 244/202 |
| 2,961,101 | 11/1960 | Hutton | 211/132.1 |
| 3,235,096 | 2/1966 | Hallock et al. | 211/149 |
| 3,713,771 | 1/1973 | Taylor et al. | 436/48 |
| 4,641,930 | 2/1987 | Podvin et al. | 359/391 |
| 4,765,469 | 8/1988 | Seifert | 206/454 |
| 4,801,431 | 1/1989 | Cuomo et al. | 359/396 |
| 5,002,736 | 3/1991 | Babbitt et al. | 359/396 |
| 5,149,244 | 9/1992 | Webber et al. | 206/454 |
| 5,350,069 | 9/1994 | Agwu | 206/456 |
| 5,641,683 | 6/1997 | Van Dusen et al. | 436/46 |
| 5,762,201 | 6/1998 | Whalen | 206/454 |

*Primary Examiner*—Thong Nguyen
*Attorney, Agent, or Firm*—Haugen Law Firm PLLP

[57] ABSTRACT

An improved receptacle or holder for microscope slides used in scientific, medical or medically related procedures, with the receptacles being configured to positionably receive, hold and index microscope slides either vertically or horizontally by means of an articulated array of individual holders. The design further minimizes slide-to-cradle contact, with the configuration allowing for rapid drainage of liquids from the slide surfaces. The cradle is also configured to facilitate manual grasping of the edge surfaces of slides being held within the cradle.

5 Claims, 8 Drawing Sheets

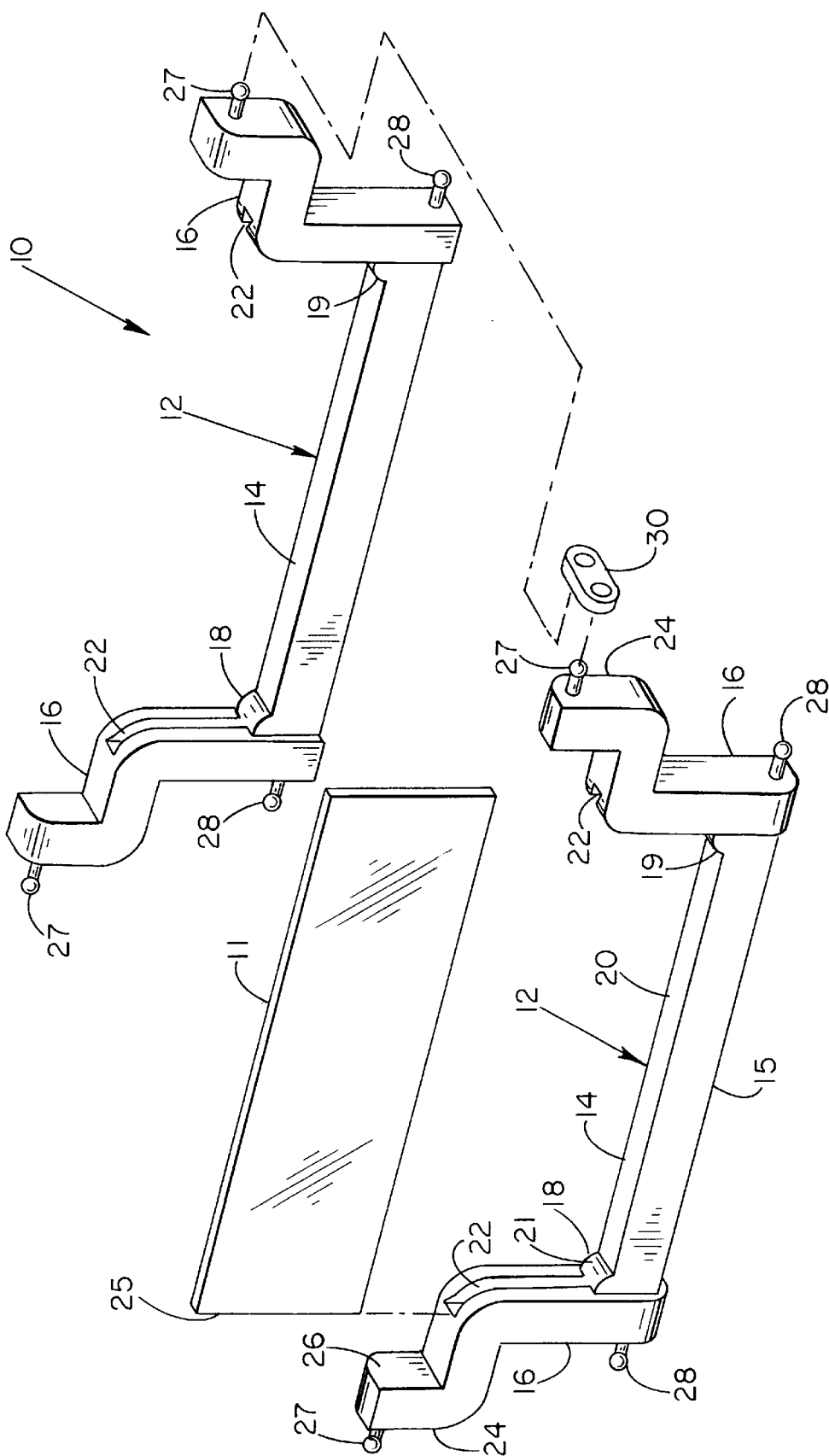

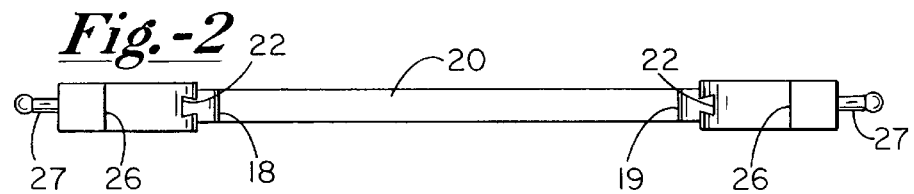
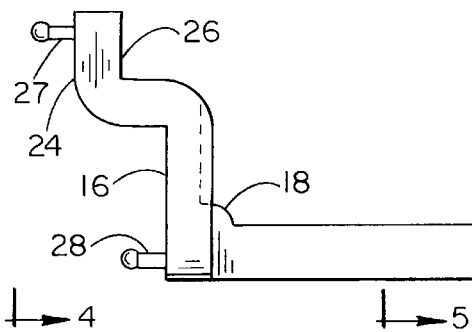
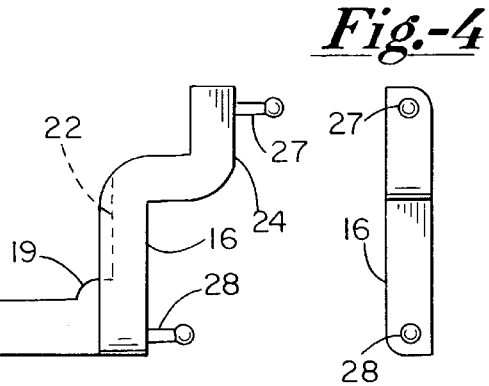
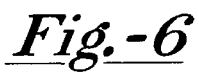
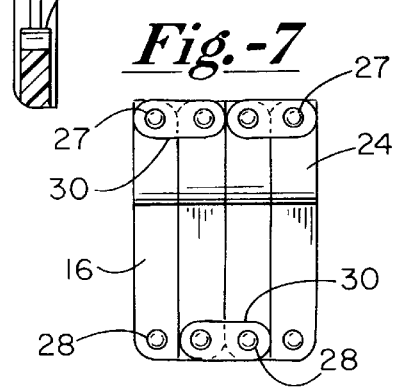
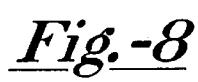
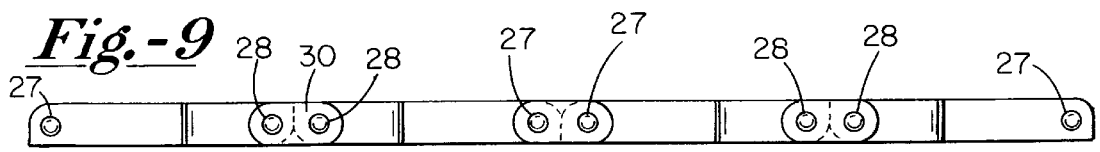

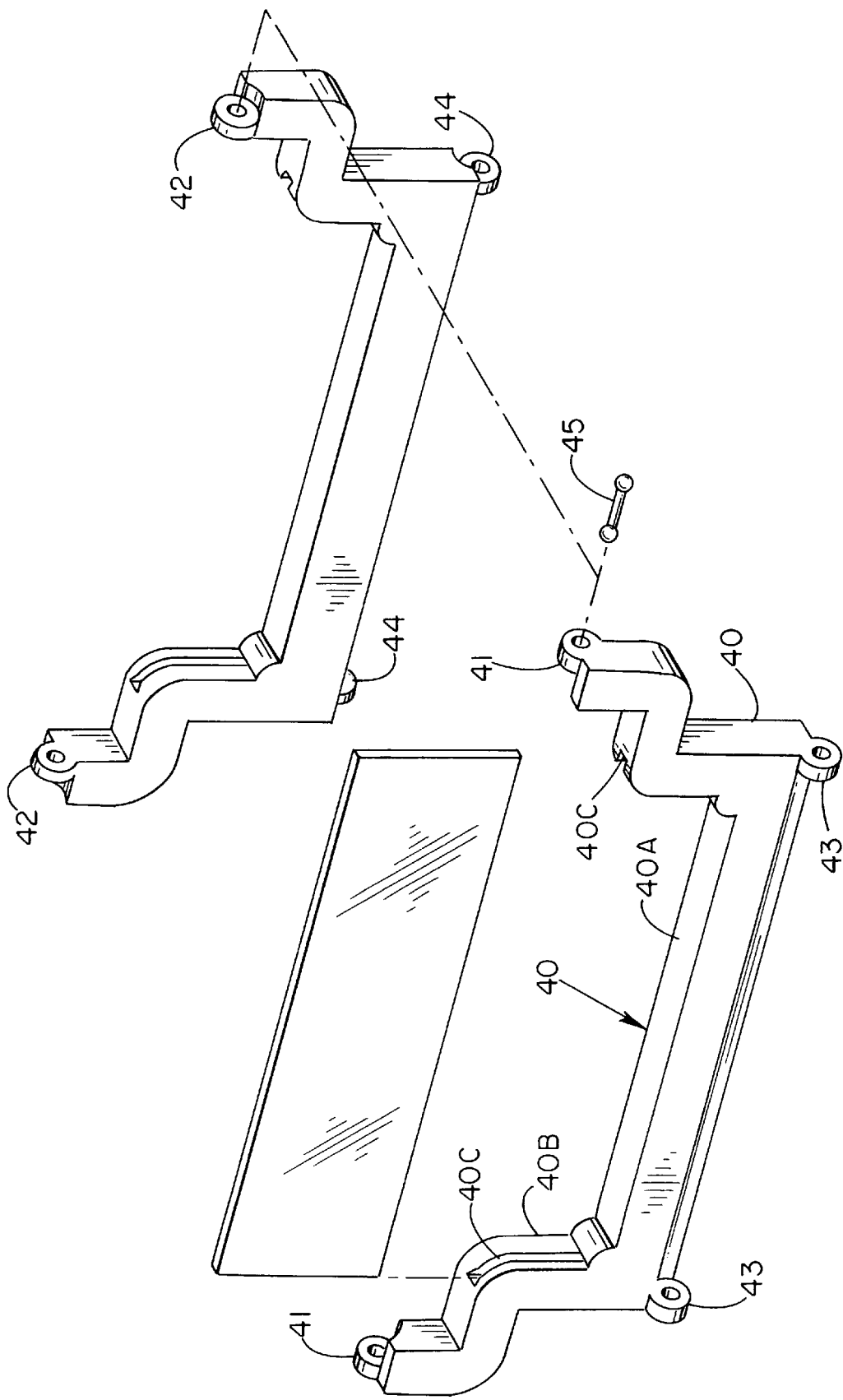

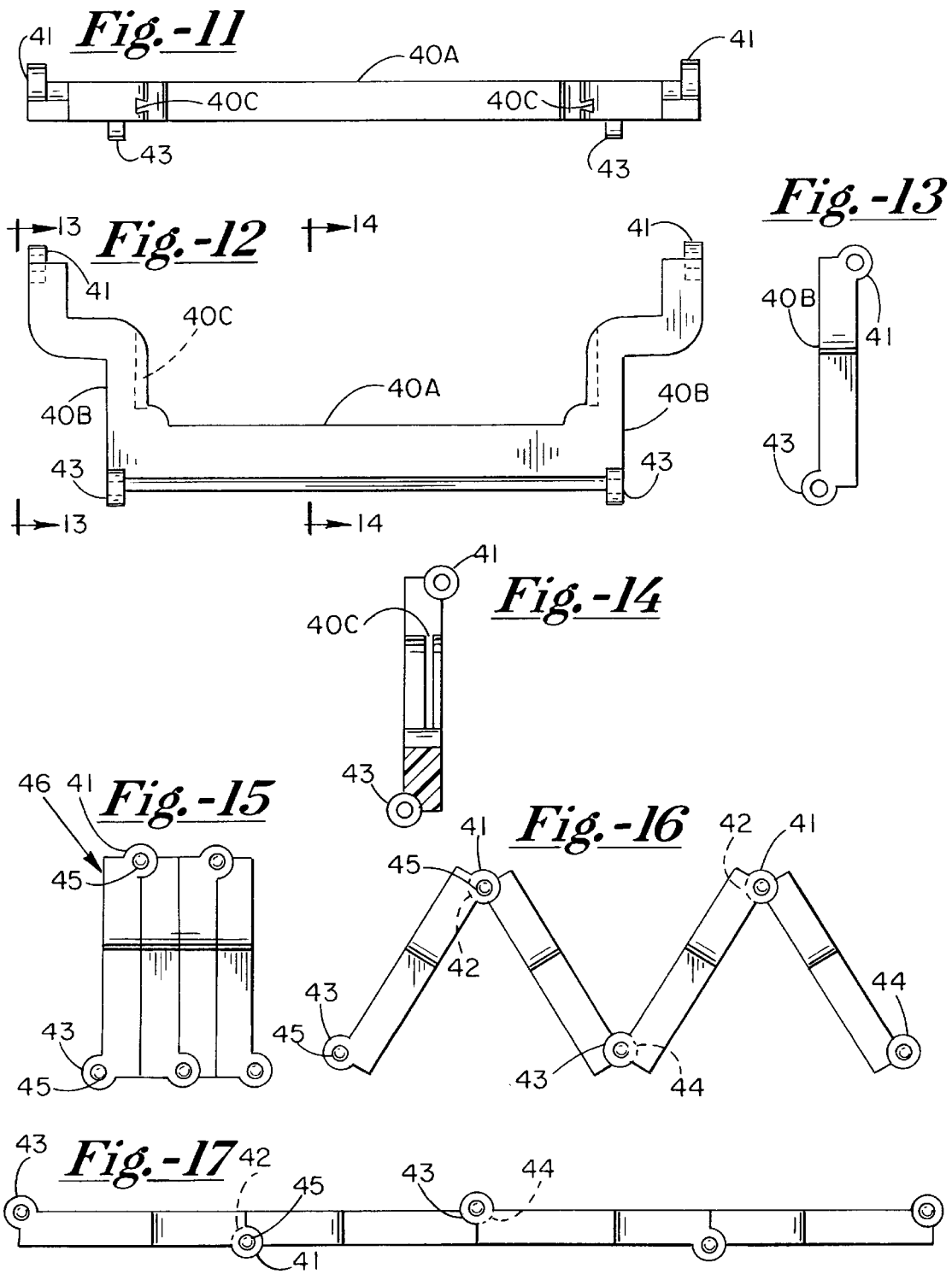

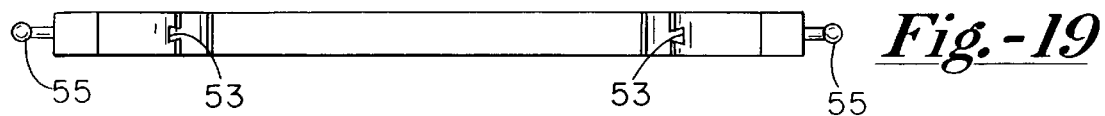
*Fig.-19*
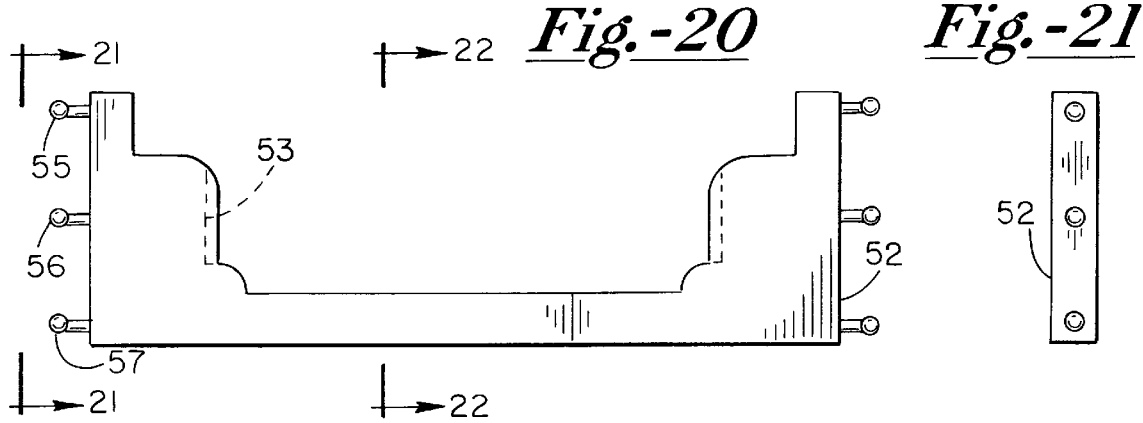
*Fig.-20*  *Fig.-21*
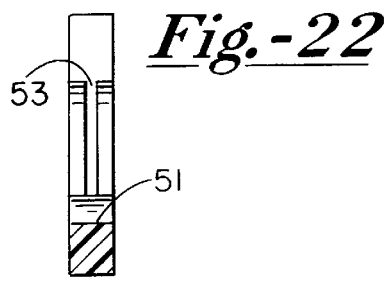
*Fig.-22*
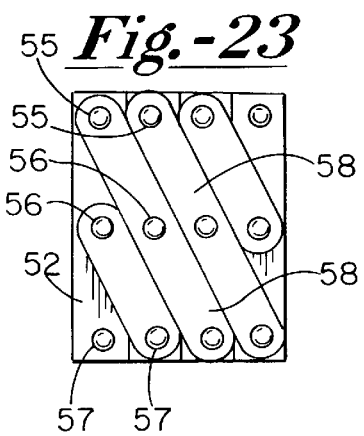
*Fig.-23*
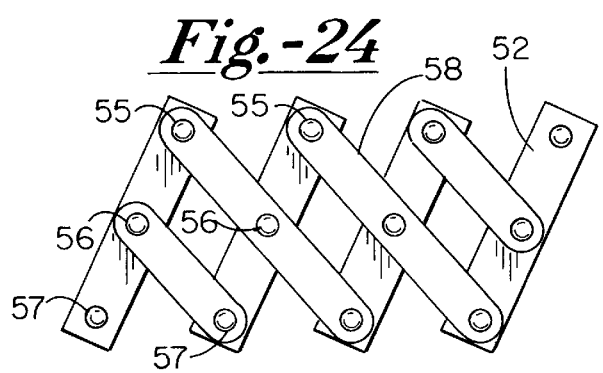
*Fig.-24*
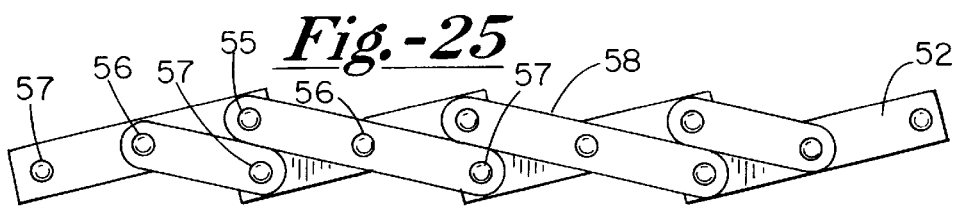
*Fig.-25*

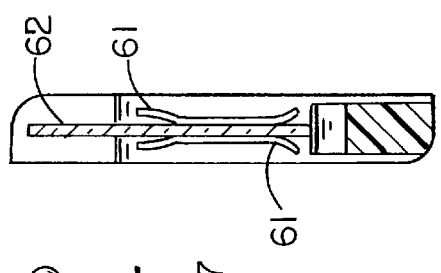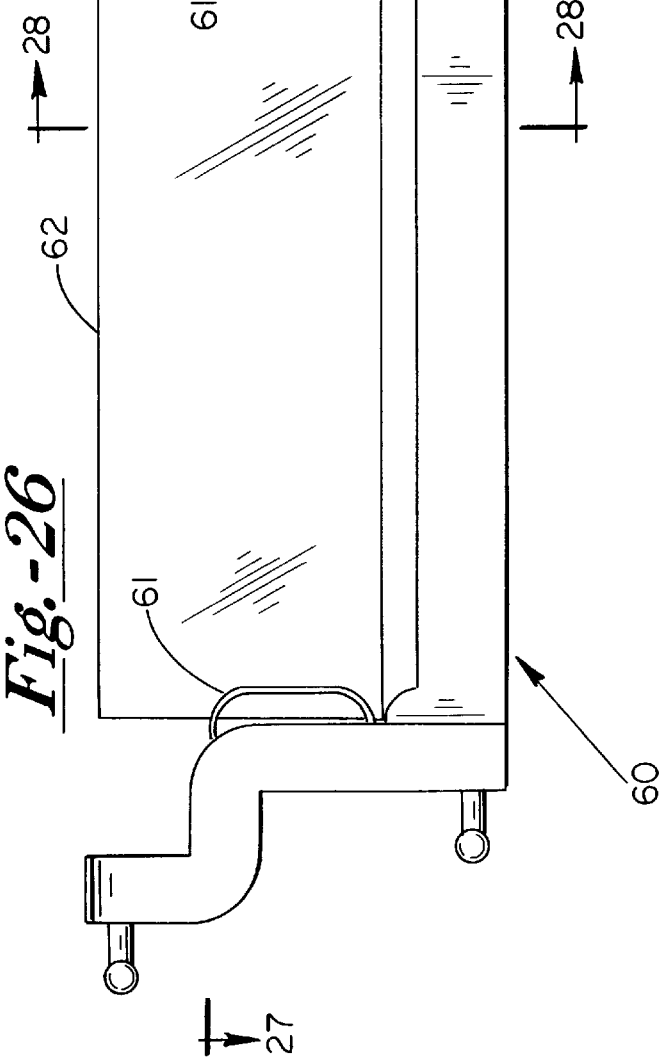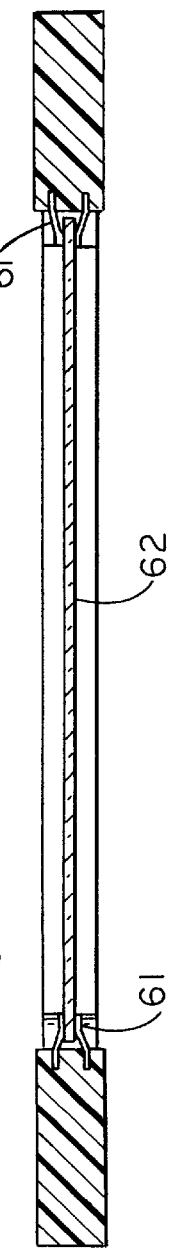

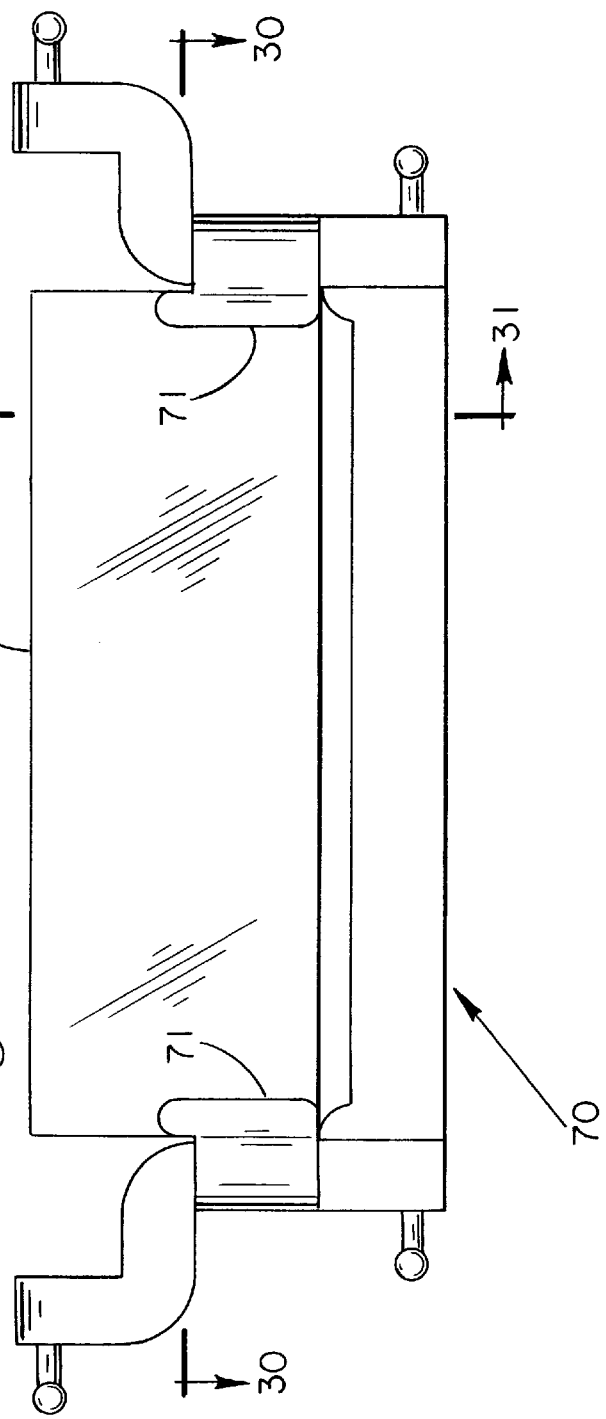

FOLDING RACK FOR MICROSCOPE SLIDES

BACKGROUND OF THE INVENTION

The present invention relates to an improved receptacle or holder for microscope slides such as those utilized for specimen retention in scientific, medical or medically related procedures. The slide receptacles of the present invention are designed to positionably receive and hold specimen retaining microscope slides in a cradle designed for minimizing slide-to-cradle contact areas while allowing for appropriate drainage of aqueous solutions therefrom, and also configured to facilitate manual grasping of the edge surfaces of slides being held within the cradle means. The cradle means of the present invention is particularly adapted for coupling individual cradles together with a linkage system to permit simultaneous articulation of a plurality of slides, so as to present the slides or groups of slides in appropriate vertical or horizontal orientation. Stated briefly, the slide receptacle or cradle means of the present invention positionably receives the slides in an appropriate array, while at the same time reduces the surface of contact between the edges of the slides and the support. Also, the configuration facilitates manual grasping or gripping of the slides along the edge surfaces.

In the past, receptacles have been provided for retaining microscope slides in predetermined or proper orientation for exposure of the slides to various operations or procedures, with the orientation depending upon the immediate application. Typical operations or procedures include exposure to washing and/or rinsing solutions, as well as exposure to various controlled environments, such as one of controlled temperature and humidity. In order to enhance and otherwise facilitate appropriate handling of the slides, the present invention provides for minimal areas or zones of contact between the slides and the holder, and further provides and facilitates manual grasping and/or gripping of the individual slides for removal and/or transfer from the holder. The configuration of the cradles of the present invention are such that the area of contact is minimized to facilitate rapid and efficient liquid drainage, such as aqueous or other solutions which typically are in contact with the slides, as well as to facilitate manual manipulation of the slides.

SUMMARY OF THE INVENTION

In accordance with the present invention, a microscope slide receptacle means is provided for positionably receiving and holding specimen retaining slides, with each slide receptacle means comprising a frame which defines a cradle for enhanced support and handling of the slides being retained. The cradle is of a generally "U"-shaped configuration with a lateral extending base support and a pair of arms extending upwardly from opposed ends of the base. The base support has a generally arcuately configured slide engaging gusset means filling the angular junction which is created between the base and each of the arms so as to position the bottom edge of the slide above the surface of the base support. In this fashion, the area or zone of contact between the base support and the slide is minimal, thereby reducing the risk of cross-contamination between the slide and its support. The upwardly extending arms have a lower slotted slide engaging segment or other engaging means along with a laterally outwardly offset portion displaced from the slotted segment portion at the upper ends thereof. This offset zone creates an open area adjacent the upper lateral edges of the slide which facilitates manual gripping of the edge surfaces of the slides being held within the cradle.

In addition, the frame means of the present invention is uniquely designed to provide a receptacle for retaining or holding the slides in registration, one with another. Appropriate registration is achieved by means of utilizing either the slotted segments, molded-in lateral clips or preformed lateral clips which are coupled to the upwardly extending arms. The clips further reduce the area of contact between the surface of the slide and surfaces of the receptacle. All of these designs allow more rapid and complete drainage of liquids from the slide, while at the same time holding the slides in accurate registration, as well as in a configuration which facilitates manual slide removal.

An additional feature of the present invention is the utilization of linkage means between mutually adjacent receptacle cradle or frame means. Specifically, linkage means are coupled from points laterally outwardly or above the cradle for simultaneous articulating arcuate rotational motion of a plurality of cradles. This linkage means is designed to provide simultaneous rotational motion, with the motion obtained from the actuation mechanism either being scissors-like, accordion-like, or pantographic-like.

Therefore, it is an object of the present invention to provide an improved microscope slide receptacle means which comprises a frame defining a support cradle, with the frame being designed to facilitate rapid drainage of liquid from the slides, and further being designed to minimize the areas of contact between the slides and the cradle.

It is a further object of the present invention to provide an improved slide receptacle means which utilizes cradles articulated for simultaneous rotational motion, with the articulation maintaining the individual slides comprising an array of slides in appropriate and desired registration.

It is yet a further object of the present invention to provide an improved receptacle system for microscope slides which facilitates removal of the slides manually.

Other and further objects and features of the present invention will become apparent to those skilled in the art upon a study of the following specification, appended claims, and accompanying drawings.

IN THE DRAWINGS

FIG. 1 is a partially exploded perspective view of a pair of cradle supports arranged in side-by-side relationship, and with a microscope slide being shown with one of the cradles, and with an appropriate linkage means being illustrated for coupling the two cradle members together, one to the other;

FIGS. 2 and 3 are top plan and front elevational views respectively of the cradle means illustrated in FIG. 1;

FIG. 4 is a side elevational view taken along the line and in the direction of the arrows 4—4 of FIG. 3;

FIG. 5 is a vertical sectional view taken along the line and in the direction of the arrows 5—5 of FIG. 3;

FIG. 6 is a fragmentary top plan view on a slightly enlarged scale, and illustrating one end of the cradle means illustrated in FIG. 1;

Figure 18:
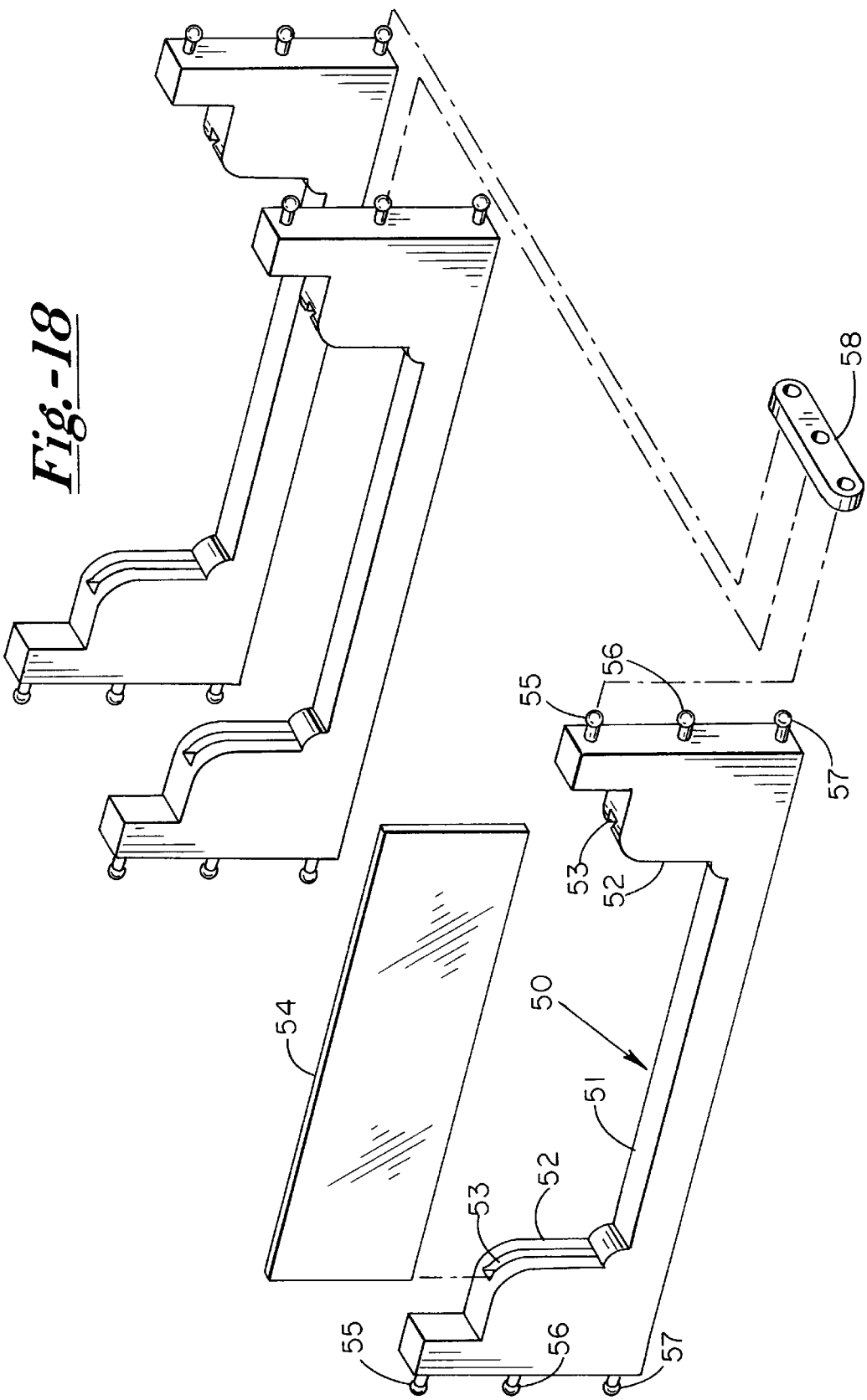

FIGS. 7, 8 and 9 are side elevational views respectively of a plurality of cradles as shown in FIG. 1, and being coupled together with appropriate linkage means to provide for simultaneous accordion-like articulating motion, with FIG. 7 illustrating the cradles in closed planar vertical array, FIG. 8 illustrating the slides in partially open array, and with FIG. 9 illustrating the individual cradles in the array in extended in-line horizontally disposed relationship;

FIG. 10 is a view similar to FIG. 1 and illustrating an alternate preferred embodiment and illustrating a modified form of linkage means to couple the individual support cradles together to accommodate scissors-like articulating motion;

FIGS. 11, 12, 13 and 14 are top plan, front elevational, side elevational, and vertical sectional views respectively of the embodiment illustrated in FIG. 10, with FIG. 13 being taken along the line and in the direction of the arrows 13—13 of FIG. 12, and with FIG. 14 being taken along the line and in the direction of the arrows 14—14 of FIG. 12;

FIG. 15 is a side elevational view of an array of cradle receptacles as illustrated in FIG. 10, with FIG. 15 illustrating the individual cradles in an array in abutting relationship, one to another;

FIG. 16 is a view similar to FIG. 15 and illustrating the scissors-like articulating motion wherein the individual cradles comprising the array are in angular disposition, one to another;

FIG. 17 is a view similar to FIG. 15 and illustrating the cradle receptacles comprising the array in an in-line horizontally disposed relationship;

FIG. 18 is a view similar to FIG. 10 and illustrating a further embodiment of the present invention, wherein the linkage means is arranged to provide pantographic-like articulating motion between individual cradle receptacles;

FIGS. 19, 20, 21 and 22 are top plan, front elevational, side elevational, and vertical sectional views respectively of the cradle receptacle means illustrated in FIG. 18;

FIG. 23 is a side elevational view of an array of cradle receptacles as illustrated in FIG. 18, with FIG. 23 illustrating the individual cradles in an array adapted for pantographic-like articulating motion;

FIG. 24 is a view similar to FIG. 23 and illustrating the cradle receptacles comprising the array in an in-line generally to vertically disposed relationship;

FIG. 25 is a side elevational view of an array of cradle receptacles, showing the cradles comprising the array in overall modified generally horizontally disposed relationship;

FIG. 26 is a front elevational view of a cradle receptacle similar to that illustrated in FIG. 3, but with the slotted segment formed in the upwardly extending arms being replaced with a molded-in wire clip for engaging a microscope slide therewithin;

FIGS. 27 and 28 are top plan and vertical sectional views respectively of the cradle means illustrated in FIG. 26;

FIG. 29 is a view similar to FIG. 26 with a snap-in metal clip being substituted for the wire clip of the device illustrated in FIG. 26 and for the slotted segment formed in the upwardly extending arms of the device of FIGS. 1–9 inclusive; and FIGS. 30 and 31 are top plan and vertical sectional views respectively of the cradle receptacle illustrated in FIG. 29.

DESCRIPTION OF THE PREFERRED EMBODIMENT

With attention being directed to FIG. 1 of the drawings, the microscope slide receptacle means generally designated 10 is provided for positionably receiving and holding specimen retaining microscope slides such as slide 11 therewithin. The receptacle means comprises a plurality of each frame means, generally designated 12 defining a cradle for supporting the slides. The frame means generally designated 12 comprises a "U"-shaped cradle 14 with a generally laterally extending base support 15 with a pair of arms 16—16 extending upwardly from opposed ends of the base support 15. The base support means is provided with arcuately configured slide engaging gussets as at 18 and 19, with gussets 18 and 19 filling the angular junction between the base 15 and each of the upwardly extending arms 16—16. This arrangement provides that substantially the entire bottom edge surface of the slide will be held above the upper surface 20 of base 15. In other words, contact between the receptacle and the bottom edge surface of the slide will be limited to substantially a line contact at the apex of the gussets 18 and 19, such as at and along the gusset surface as at 21. Arms 16—16 are provided with a slot as at 22—22 along the lower ends thereof. A laterally offset portion as at 24—24 is provided at the upper ends of arms 16—16 in order to permit manual gripping of the edge surfaces of slides held within the cradle. The zone for finger access is provided between the outer lateral edge of slide 11 as at 25, and the inner surface 26 of offset portion 24.

In order to permit appropriate articulation of the cradle means, trunnions such as at 27—27 and 28—28 are provided. Linking means such as link 30 are provided for interconnecting upper trunnions 27—27 from adjacent cradles together, along with a similar linkage means being provided to interconnect trunnions 28—28 together. As indicated in FIG. 7, the individual links 30—30 are offset so as to provide for articulating accordion-like motion as indicated in FIGS. 8 and 9.

In order to provide for proper lateral support for microscope slides, attention is directed to FIGS. 2, 5 and 6 of the drawings, wherein slot 22 is illustrated in slightly enlarged scale. This view illustrates the configuration of the channel so as to reduce areas of mutual contact.

Attention is now directed to FIG. 10 of the drawings wherein an alternate form or configuration of cradle receptacle 40 is illustrated including a base 40A and upwardly extending arms 40B—40B. In this arrangement, laterally offset pin-receiving ears or bushings are provided as shown at 41—41, 42—42, 43—43 and 44—44. A pin, rivet, or other retainer, such as pin 45 is designed to be inserted into the mating bores such as between ears or bushings 41—41 and 42—42 respectively. Similarly, pin 45 may be received in ears or bushings formed as at 43—43 and 44—44. The configuration of base 40A and upwardly extending arms 40B—40B is the same as that illustrated in the embodiment of FIGS. 1–9, with the exception of the slide receiving slots 40C—40C, which are offset.

Additional detail of this configuration or design including the offset slots are illustrated in FIGS. 11–14 inclusive.

In order to articulate an array of cradle receptacles, such as array generally designated 46 in FIG. 15, adjacent cradle supports as at 40—40 are shown. In this arrangement, the articulating motion is provided as between mutually coupled ears so as to provide scissors-like motion as illustrated in FIGS. 16 and 17, with the offset slots facilitating the motion and positioning of the slides.

With attention being directed to FIG. 18, a still further embodiment is illustrated which provides a different linkage means for a modified form of motion, namely pantographic-like motion. In this connection, each cradle 50 is provided with a base 51 along with laterally arranged upwardly extending arms 52—52. Slots are provided along the inner surfaces of arms 52—52 as at 53—53 in the same manner as that of the prior embodiment of FIGS. 1–9. Microscope slide 54 is received within slots 53—53. The arrangement and configuration of cradle 50 is essentially the same as that of the prior embodiment of FIGS. 1–9, with the exception of the linkage means. In this connection, the linkage means consists of three groups of laterally extending pins such as at 55—55, 56—56 and 57—57. Linkage means such as link 58 are provided to extend between adjacent cradle receptacles, particularly as illustrated in FIGS. 23, 24 and 25. The arrangement is such that the center-to-center of bores formed in link 58 are the same distances as between adjacent pins 55—55, 56—56, and 57—57 respectively. With this arrangement, the pantographic-like motion or articulation shown in FIGS. 23–25 inclusive is obtained.

With attention now being directed to FIGS. 26, 27 and 28, a modified form of cradle receptacle is illustrated. Each cradle is generally designated 60 and is provided with molded-in wire clips as at 61—61, with clips 61—61 being designed to grip slide 62. Clips 61—61 are provided in lieu of the slots such as are formed at 22 and 53 in previously disclosed embodiments hereinabove. Other than the substitution of the clips 61—61 for the grooves or slots, the configuration of cradle receptacle 60 is the same as that of cradle receptacle support or frame 10 illustrated in FIGS. 1–9.

With attention now being directed to FIGS. 29, 30 and 31, each cradle receptacle is generally designated 70 and is provided with a pair of laterally disposed snap-in metal clips 71—71 for gripping the lateral edges of microscope slide 72. Except for the substitution of clips 71—71 for slots 22—22 and 53—53, the configuration of cradle receptacle 70 is similar to that of cradle receptacle 10 in the embodiment of FIGS. 1–9 hereinabove.

In actual usage, the user introduces the specimen retaining microscope slide or slides such as slides 11, 62 and 72 in place within a cradle. When properly positioned within the cradle receptacle, the slides may be treated through exposure to appropriately selected liquids such as aqueous solutions or rinses, and may also be exposed to appropriately selected environments within a chamber or other enclosure. These are typical operations for which microscope slides are normally employed, as known to those of skill in the art. Thereafter, the individual slides may be gripped manually for removal for study, subsequent exposure, cleaning, and/or other purposes as indicated by the specific application or operation. In working with arrays of slides, the articulating mechanisms as disclosed herein may be employed to position the slides in desired relative relationship, one to another. As indicated hereinabove, the folded-flat array configurations are available with each design, and each design further provides appropriate mechanisms for holding the slides in desired registration.

It will be appreciated that various modifications may be made to the embodiments illustrated herein without actually departing from the spirit and scope of the present invention.

What is claimed is:

1. Microscope slide receptacle means for positionably receiving and holding specimen retaining microscope slides and comprising a frame means defining a plurality of cradles wherein each cradle supports a slide having a bottom edge surface and side edge surfaces therewithin, said frame means being characterized in that:

(a) each cradle of said frame means comprising a generally "U"-shaped cradle with a generally laterally extending base support with an upper surface and with a pair of arms, each arm extending upwardly from opposed ends of said base support and forming an angular junction therewith; and (b) each of said opposed ends having a generally arcuately configured slide engaging gusset means coupled thereto for filling the said angular junction between said base and each of said arms so as to position substantially the entire bottom edge surface of a slide held therein above and in spaced relationship to said upper surface of said base support; and (c) each of said upwardly extending arms having a slotted slide engaging segment along a lower end thereof and a laterally offset portion displaced outwardly from said slotted segment at an upper end thereof so as to permit manual gripping of the edge surfaces of a slide held within said cradle.

2. The frame means of claim 1 being further characterized in that a plurality of cradle means are provided with linkage means being coupled laterally outwardly thereof for simultaneous articulating arcuate motion of each of said plurality of cradles, allowing the slides to be presented vertically or horizontally without being removed from one of said slide support cradles.

3. The frame means as defined in claim 2 being particularly characterized in that said linkage means creates simultaneous accordion-like articulating motion.

4. The frame means as defined in claim 2 being particularly characterized in that said linkage means creates simultaneous scissors-like articulating motion.

5. The frame means as defined in claim 2 being particularly characterized in that said linkage means creates simultaneous pantographic-like articulating motion.

* * * * *